US00PP32000P2

(12) United States Plant Patent
Dabadie

(10) Patent No.: US PP32,000 P2
(45) Date of Patent: Jul. 21, 2020

(54) ***LAGERSTROEMIA* PLANT NAMED 'DABLAGE01'**

(50) Latin Name: *Lagerstroemia indica*
Varietal Denomination: DABLAGE01

(71) Applicant: Alain Dabadie, Hagetmau (FR)

(72) Inventor: Alain Dabadie, Hagetmau (FR)

( * ) Notice: Subject to any disclaimer, the term of this patent is extended or adjusted under 35 U.S.C. 154(b) by 0 days.

(21) Appl. No.: 16/501,309

(22) Filed: Mar. 22, 2019

(51) Int. Cl.
*A01H 5/02* (2018.01)
*A01H 6/00* (2018.01)

(52) U.S. Cl.
USPC ..... Plt./252

(58) Field of Classification Search
USPC ..... Plt./252, 226
CPC ... A01H 5/02; A01H 5/00; A01H 5/04; A01H 6/00
See application file for complete search history.

(56) References Cited

PUBLICATIONS

Floral Daily Part 3: Novelties at Plantarium 2017 [online] retrieved Nov. 20, 2019, retrieved from the Internet at https://www.floraldaily.com/article/9011274/novelties-at-plantarium-2017/, pp. 1,13,22 (3 pages total). (Year: 2017).*
Gu et al. *Lagerstroemia densa* (Lythraceae), a new species from Daqing Mountain, Guangxi Zhuang Autonomic Region, China, Phytotaxa 204 (3): 230-234, 2015. (Year: 2015).*
Upov Pluto Plant Variety Database Nov. 19, 2019 [online] retrieved Nov. 20, 2019, retrieved from the Internet at https://www3.wipo.int/pluto/user/en/index.jsp, one page (Year: 2019).*

* cited by examiner

*Primary Examiner* — June Hwu
(74) *Attorney, Agent, or Firm* — Cassandra Bright

(57) ABSTRACT

A new and distinct *Lagerstroemia* cultivar named 'DABLAGEO1' is disclosed, characterized by early blooming, and observed mildew resistance. Plants flower prolifically, producing bright red-purple flowers. The new variety is a *Lagerstroemia*, normally used for outdoor ornamental purposes.

2 Drawing Sheets

Latin name of the genus and species: *Lagerstroemia indica.*

Variety denomination: 'DABLAGE01'.

BACKGROUND OF THE INVENTION

The new *Lagerstroemia* cultivar is a product of a planned breeding program conducted by the inventor, Alain Dabadie, in Hagemau, France. The objective of the breeding program was to develop *Lagerstroemia* cultivars exhibiting the characteristics of early, abundant flowering and mildew resistance. The open pollination resulting in this new variety was made during August of 2010.

The seed parent is the unpatented commercial variety referred to as *Lagerstroemia* 'Houston'. The pollen parent is unknown. The new variety was selected September of 2011 by the inventor in a group of seedlings resulting from the 2009 open pollination, in a seedling trial field in Landes, France.

Asexual reproduction of the new cultivar was performed by softwood cuttings. This was first performed at a commercial nursery in Landes, France during February of 2011 and has shown that the unique features of this cultivar are stable and reproduced true to type in multiple successive generations.

SUMMARY OF THE INVENTION

The cultivar 'DABLAGE01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DABLAGE01' These characteristics in combination distinguish 'DABLAGE01' as a new and distinct *Lagerstroemia* cultivar;

1. Bright red-purple flowers.
2. Prolific flowering.
3. Early blooming.
4. Resistance to mildew.

Plants of the new cultivar 'DABLAGE01' are similar to plants of the seed parent in most horticultural characteristics; however, plants of the new cultivar 'DABLAGE01' differ in the following;

1. The new variety has a brighter pink colored flower.
2. The new variety produces inflorescences approximately 16 to 30 cm long, compared to the 10 to 16 cm inflorescences of the parent variety.
3. The new variety has resistance to mildew, the seed parent has not been observed to have resistance under same cultural conditions.
4. The new variety begins flowering mid-June to early July, under the same conditions the parent variety begins flowering mid-July.

The pollen parent cannot be identified.

COMMERCIAL COMPARISON

Plants of the new cultivar 'DABLAGE01' are comparable to the commercial variety *Lagerstroemia* 'Pecos', unpatented. The two *Lagerstroemia* varieties are similar in most horticultural characteristics, including observed mildew resistance, however, the new variety 'DABLAGEO1' differs in the following;

1. The new variety has a brighter pink flower.
2. New variety produces longer inflorescences.
3. New variety has a more weeping habit than the fully upright habit of 'Pecos'.

BRIEF DESCRIPTION OF THE PHOTOGRAPHS

Figure 1:
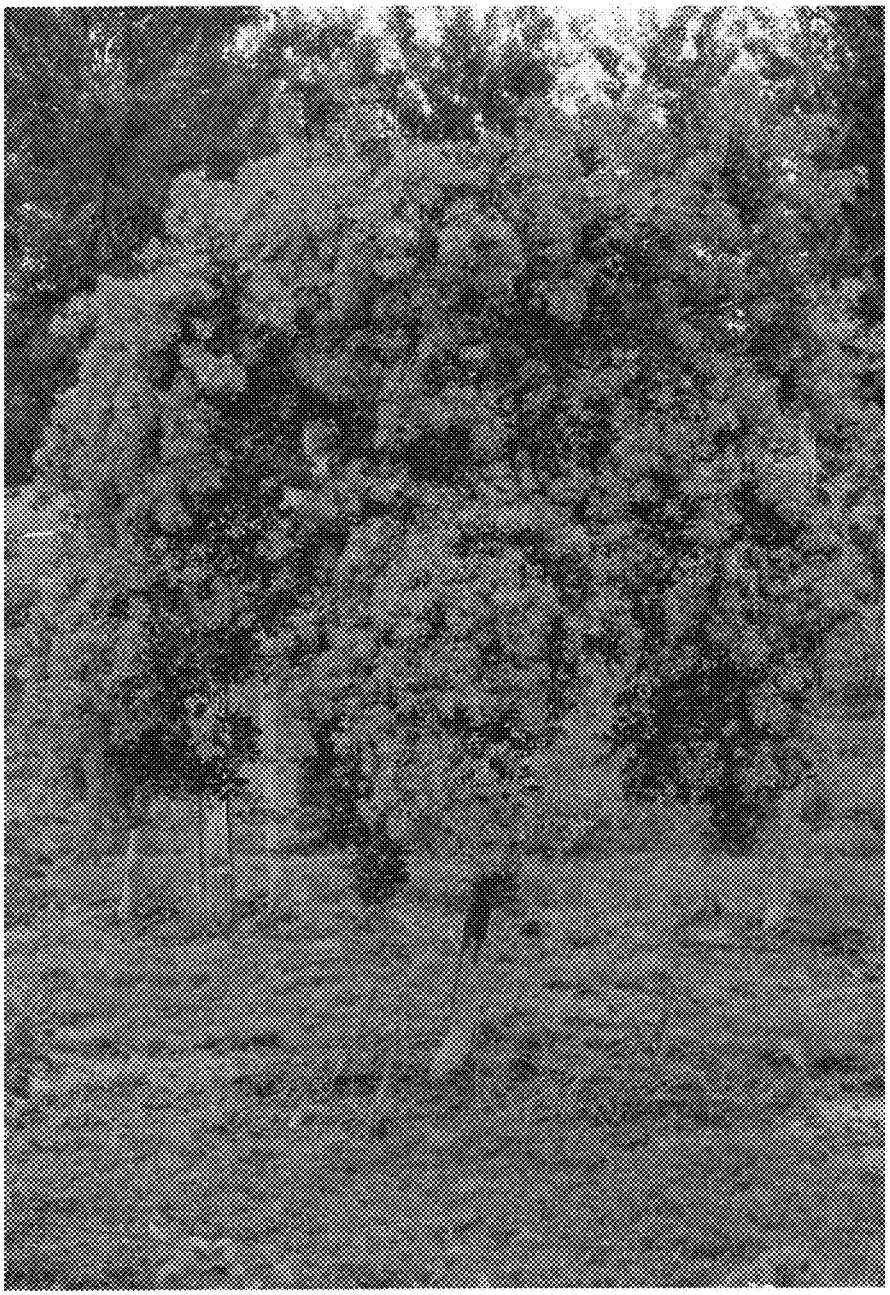

The accompanying photograph in FIG. 1 illustrates, in full color, a typical grafted form of weeping standard plant habit of 'DABLAGE01' grown outdoors in Landes, France in the ground. The rootstock is an unnamed *Lagerstroemia indica*. Age of the plant photographed is approximately 5 years old from a rooted cutting.

Figure 2:
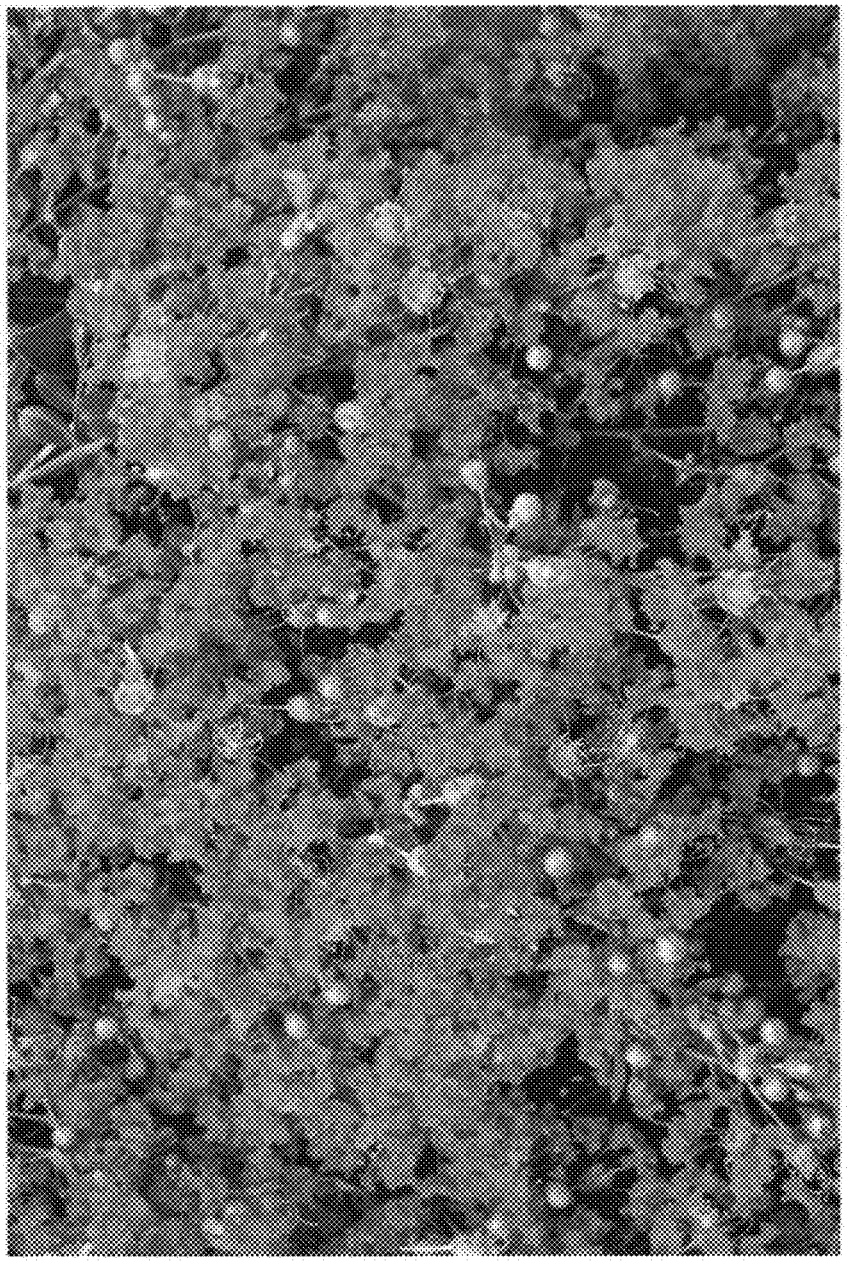

FIG. 2 illustrates a close up view of the flowers. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'DABLAGE01' plants outdoors during July of 2018 in Landes, France and measured during the Summer. The growing temperature ranged from approximately 8° C. to 32° C. during the day and from approximately 1° C. to 12° C. during the night. General light conditions are normal sunlight and numerical values represent averages of typical plant types.

Botanical classification: *Lagerstroemia indica* 'DABLAGE01'.

PROPAGATION

Type of propagation typically used: Terminal vegetative cutting.

Time to initiate roots: About 14-21 days at about 24° C.

Time to produce a rooted cutting: About 28-35 days at about 24° C.

Root description: Thin fibrous, not fleshy, freely branching. White in color, not accurately measured with RHS Chart.

PLANT

Age of plant described: 2-3 years old from a rooted cutting.

Container size: 3 gallon container.

Overall plant shape: Small tree, with a weeping form when grown as a grafted standard. Dense, semi-prostrate arching when grown as a shrub.

Growth habit: Freely branching.

Plant spread: 100 cm.

Plant height: 200 cm when grafted and grown as a standard. About 100 cm when grown as a shrub.

Growth rate: Moderate

Plant vigor: Good.

Branching habit: Free branching.

Length of primary lateral branches: Varies as this is often pruned. 20 to 50 cm on average.

Diameter of lateral branches: 7 to 12 mm.

Quantity of lateral branches: About 20.

Stem:

*Color.*—New growth: Green group 135B. Old growth: Grey brown group 199A.

*Shape.*—Round.

*Strength.*—Good.

*Aspect angle.*—Arching.

*Texture.*—Pubescent, then woody with age.

Internode length: Average range 3.5 to 5.0 cm.

Bark peel: Not observed to peel or produce a different color than the branches.

FOLIAGE

Leaf:

*Arrangement.*—Opposite or sub-opposite.

*Average length.*—6.0 cm.

*Average width.*—3.0 cm.

*Shape of blade.*—Elliptical.

*Apex.*—Acute.

*Base.*—Obtuse.

*Margin.*—Entire.

*Texture of top surface.*—Smooth.

*Texture of bottom surface.*—Smooth.

*Color.*—Young foliage upper side: Green group 137B. Young foliage under side: Green group 137D. Mature foliage upper side: Green group 137A. Mature foliage under side: Green group 137C.

*Venation.*—Type: Pinnate. Venation color upper side: Green 138B. Venation color under side: Green 138B.

*Petiole.*—Length: 1 mm. Diameter: 1 mm. Texture, upper side: Smooth. Texture, under side: Smooth. Color, upper side: Green 138B. Color, under side: Green 138B.

FLOWER

Natural flowering season: Begins flowering Mid June and early July in Landes, France. Flowers all Summer.

Inflorescence form: Panicles.

Flowers per inflorescence: About 100 to 200 flowers and buds.

Inflorescence size:

*Width.*—10 cm.

*Length.*—Average range 15 to 30 cm.

Individual flowers:

*Type.*—Rotate.

*Shape.*—Obovate.

*Habit.*—Whorled outward.

*Diameter.*—4.0 cm.

*Length.*—4.0 cm.

*Depth.*—2.0 cm.

*Persistence.*—Self-cleaning.

*Fragrance.*—Floral, very light.

Petals:

*Arrangement.*—Whorled.

*Number.*—6.

*Shape.*—Loosely edged and undulate orbit shape.

*Margin.*—Loose, undulate.

*Tip shape.*—Rounded.

*Base shape.*—Rounded.

*Length.*—1.9 cm.

*Width.*—1.6 cm.

*Texture.*—Upper: Soft, smooth, delicate. Lower: Soft, smooth, delicate.

*Color.*—When opening: Upper surface: Near RHS Red-Purple 58A. Under surface: Near RHS Red-Purple 58A. Fully opened: Upper surface: Near RHS Red-Purple 58B. Under surface: Near RHS Red-Purple 58B.

Bud:

*Shape.*—Sphere.
*Length.*—1.8 cm.
*Diameter.*—1.8 cm.
*Color.*—Near RHS Red-Purple 65C.

Sepals:

*Appearance.*—Smooth, glossy, fused.
*Arrangement.*—Rotate, fused.
*Shape.*—Narrowly triangular.
*Tip shape.*—Acute.
*Base shape.*—Obtuse.
*Margin.*—Entire.
*Quantity per flower.*—6.
*Length.*—12 mm.
*Width.*—5 mm.
*Margin.*—Entire.
*Texture.*—Upper: Smooth, coriaceous, rugose. Lower: Smooth.
*Color.*—Upper: Green 138C. Lower: Green 138D.

Calyx:

*Shape.*—Fused into a conical shape.
*Length.*—14 mm.
*Diameter.*—12 mm.

Peduncle:

*Length.*—1 cm.
*Diameter.*—1 mm.
*Texture.*—Smooth.
*Color.*—Green 138C blended with Red-Purple 58A.
*Orientation.*—Upright and outward.
*Strength.*—Strong and flexible.

Pedicel:

*Length.*—1.5 cm.
*Diameter.*—18 mm.
*Angle.*—About 45 degrees from attachment.
*Strength.*—Moderate.
*Texture.*—Smooth, slightly pubescent.
*Color.*—Near Red-Purple 63C.

REPRODUCTIVE ORGANS

Stamens:

*Number.*—About 30.
*Filament length.*—1 cm.
*Filament color.*—White 155D.

Anthers:

*Shape.*—Linear.
*Length.*—1 mm.
*Color.*—Yellow group 13A.
*Pollen.*—Amount: Moderate. Color: Yellow 13A.

Pistil:

*Number.*—1.
*Length.*—1.5 cm.

Stigma:

*Shape.*—Globe.
*Color.*—Near RHS Red-Purple 58A.
*Ovary color.*—Green-yellow 1D.

OTHER CHARACTERISTICS

Fruits and seeds: Not observed to date.

Disease/pest resistance: Observed resistance to mildew, assumed to be the pathogen *Erysiphe australiana*. Neither resistance nor susceptibility to other normal diseases and pests of *Lagerstroemia* observed.

Temperature range: Observed to tolerate a temperature range from −10° C. to 38° C.

What is claimed is:

1. A new and distinct cultivar of *Lagerstroemia* plant named 'DABLAGE01' as herein illustrated and described.

* * * * *